United States Patent
Olsen et al.

(10) Patent No.: US 8,491,547 B2
(45) Date of Patent: Jul. 23, 2013

(54) SEPTUM MONITORING SYSTEM AND METHOD FOR AN IMPLANTABLE THERAPEUTIC SUBSTANCE DELIVERY DEVICE

(75) Inventors: James M. Olsen, Plymouth, MN (US); Charles R. Rogers, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1340 days.

(21) Appl. No.: 11/413,820

(22) Filed: Apr. 28, 2006

(65) Prior Publication Data
US 2007/0255235 A1 Nov. 1, 2007

(51) Int. Cl.
*A61M 37/00* (2006.01)

(52) U.S. Cl.
USPC ................. 604/288.02; 604/513

(58) Field of Classification Search
USPC ........ 604/9, 93.01, 175, 201, 288.01–288.04, 604/318, 404, 890.1, 891.1, 204, 116; 600/549; 137/551, 556, 558; 128/898, 899, 897; 116/202; 374/135, 138, 141, 147, 148; 702/130, 131
See application file for complete search history.

(56) References Cited

U.S. PATENT DOCUMENTS

| | | | |
|---|---|---|---|
| 4,222,374 A * | 9/1980 | Sampson et al. | 128/899 |
| 4,573,994 A | 3/1986 | Fischell et al. | |
| 4,760,837 A | 8/1988 | Petit | |
| 4,784,646 A * | 11/1988 | Feingold | 604/175 |
| 4,804,054 A | 2/1989 | Howson et al. | |
| 5,006,115 A | 4/1991 | McDonald | |
| 5,009,644 A | 4/1991 | McDonald | |
| 5,171,228 A | 12/1992 | McDonald | |
| 5,375,596 A | 12/1994 | Twiss et al. | |
| 5,957,890 A | 9/1999 | Mann et al. | |
| 6,254,548 B1 * | 7/2001 | Ishikawa et al. | 600/549 |
| 6,305,381 B1 * | 10/2001 | Weijand et al. | 128/899 |
| 6,740,076 B2 | 5/2004 | Hoben et al. | |
| 7,232,429 B2 * | 6/2007 | Moreci | 604/288.01 |
| 7,366,571 B2 * | 4/2008 | Armstrong | 607/45 |
| 2003/0114903 A1 * | 6/2003 | Ellingboe | 607/104 |
| 2004/0073196 A1 | 4/2004 | Adams et al. | |
| 2004/0122420 A1 * | 6/2004 | Amoah | 606/34 |
| 2004/0249336 A1 * | 12/2004 | Faries et al. | 604/28 |
| 2005/0070845 A1 * | 3/2005 | Faries et al. | 604/98.01 |
| 2005/0187515 A1 | 8/2005 | Varrichio | |
| 2005/0256451 A1 | 11/2005 | Adams et al. | |
| 2006/0089619 A1 | 4/2006 | Ginggen | |
| 2007/0152813 A1 * | 7/2007 | Mathur et al. | 340/539.22 |
| 2007/0239381 A1 * | 10/2007 | Ginggen et al. | 702/100 |

* cited by examiner

*Primary Examiner* — Kami A Bosworth
(74) *Attorney, Agent, or Firm* — Dicke, Billig & Czaja, PLLC (57) ABSTRACT

A system for monitoring an implantable medical device. The system includes an implantable therapeutic substance delivery device for delivering a therapeutic substance, along with a temperature sensor and an indicator device. The delivery device includes a housing maintaining a reservoir for containing the therapeutic substance. Further, the delivery device includes a fill port assembly having a port chamber in fluid communication with the reservoir and including a septum fluidly sealing the chamber. The temperature sensor is associated with the fill port assembly. Finally, the indicator device is adapted to indicate presence of a needle within the port chamber based upon information from the temperature sensor.

32 Claims, 6 Drawing Sheets

SEPTUM MONITORING SYSTEM AND METHOD FOR AN IMPLANTABLE THERAPEUTIC SUBSTANCE DELIVERY DEVICE

BACKGROUND OF THE INVENTION

The present invention relates to implantable medical devices for delivering a liquid therapeutic substance to a delivery site within a patient. More particularly, it relates to systems and methods for sensing insertion of a needle into a septum port assembly provided with an implantable therapeutic substance delivery device.

A variety of implantable medical devices are available for treating patients. For example, an implantable therapeutic substance delivery devices are typically used to deliver infusion media or therapeutic substances (such as medication) to a patient at a regulated dosage. The implantable therapeutic substance delivery device (sometimes referred to as a drug pump or medicament pump) is implanted by a clinician into a patient at a location appropriate for the therapy. Typically, an infusion catheter is connected to an outlet of the device, and is implanted/positioned to infuse the therapeutic substance at the desired therapy site so as to treat a condition such as pain, spasticity, cancer, neurodegenerative diseases, trauma, diabetes, or other medical conditions. The term "implantable therapeutic substance delivery device" as used herein refers to any implantable device for delivering medicaments including, but not limited to, bladder pumps, accumulator pumps, fixed-rate bellows pumps, and the like, as well as implantable devices that do not necessarily include a pump.

In general terms, the implantable therapeutic substance delivery device commonly includes a drug reservoir containing a volume of the infusion media, along with a pump and/or metering mechanism to propel the infusion media in some metered or constant flow dosage to the desired location from the reservoir via the catheter. Over time, the therapeutic substance in the reservoir becomes depleted and it is necessary to refill the device with a new supply of therapeutic substance. In order to avoid the need for surgery to access and refill the device, it is desirable to have the ability to percutaneously refill the drug reservoir. This is commonly done by providing the delivery device with a fill port assembly that establishes fluid access to the drug reservoir from an exterior of the device. In this regard, a resilient, resealable septum is provided with the fill port assembly, and is accessible by percutaneously inserting a hypodermic needle through the skin and then the septum. Once the septum has been pierced, the hypodermic needle is fluidly connected to the drug reservoir such that the reservoir can be refilled. Additional septum-type ports can also be provided, such as a catheter access port.

Because the device is implanted within the patient and cannot be seen directly, care must be taken to ensure that the needle is properly placed into the fill port assembly before transferring liquids. If the needle is not located within the fill port assembly (e.g., is mistakenly inserted into the catheter access port, the needle does not pierce the septum, etc.), delivery of the infusion media through the needle can result in immediate delivery of a significant quantity of the drug to the patient, with potentially dire consequences. In addition, unintended failure to properly refill the drug reservoir may lead to significant complications for the patient when the needed medication is not dispensed at a later time.

In light of the above, efforts have been made to identify to the clinician a location of the fill port assembly relative to the patient's skin prior to insertion of the needle. For example, templates are well known, and can provide a general indication or map of the fill port location following palpating the device's periphery through the patient's skin. Additionally, electronic and/or magnetic systems have been suggested that provide the clinician with additional information generally indicative of the fill port assembly position. Regardless of how the clinician arrives at an initial estimation of fill port assembly location, upon inserting the needle through the patient's skin, the clinician normally must make a manual/tactile determination as to whether the needle tip has been correctly directed to the fill port assembly and has subsequently pierced through the septum. Most clinician's are relatively comfortable in making this determination as, based on experience, the clinician can tactilely sense or feel when the needle has been inserted through the septum. However, it is sometimes difficult to know with certainty whether the septum has been accessed, especially with thick-skinned patients. Further, as implantable therapeutic substance devices become increasingly reduced in size, the attendant tactile feedback will diminish.

In light of the above, a need exists for a needle-in-septum sensor for an implantable therapeutic substance delivery device, along with an indicator device for providing the clinician with a confirmation of desired needle positioning relative to the fill port.

SUMMARY OF THE INVENTION

Aspects in accordance with principles of the present invention relate to a system for monitoring an implantable medical device. In this regard, the system includes an implantable therapeutic substance delivery device for delivering a therapeutic substance to a delivery site of a patient, along with a temperature sensor and an indicator device. The delivery device includes a housing maintaining a reservoir for containing the therapeutic substance. Further, the delivery device includes a fill port assembly having a port chamber in fluid communication with the reservoir and including a septum fluidly sealing the chamber. The temperature sensor is associated with the fill port assembly. Finally, the indicator device is adapted to indicate presence of a needle within the port chamber based upon information from the temperature sensor. In one embodiment, the system further includes a detection circuit adapted to detect the presence of a needle in the fill port assembly based upon information from the temperature sensor, as well as to prompt operation of the indicator device upon detecting or determining needle presence. In another related embodiment, the detection circuit is adapted to compare a current temperature as sensed by the temperature sensor with a set point temperature, such that when a liquid at room temperature is injected into the port chamber, the detection circuit will identify a decrease in the temperature being sensed by the temperature sensor, and interpret this decrease in temperature as being indicative of a needle being within the port chamber. In yet other embodiments, the indicator device is an audible sound generator maintained by the delivery device housing. In other embodiments, the indicator device is a display screen associated with an external controller.

Other aspects in accordance with principles of the present invention relate to a method of monitoring an implantable therapeutic substance delivery device. The method includes providing an implantable therapeutic substance delivery device for delivering a liquid therapeutic substance to a delivery site of a patient, and including a housing and a fill port assembly. The housing maintains a reservoir for containing the therapeutic substance. The fill port assembly includes a septum fluidly sealing a port chamber otherwise in fluid communication with the reservoir. With this in mind, the method includes sensing information relating to a temperature of the port chamber. Subsequently, a determination is made as to whether this sensed information is indicative of the presence of a needle within the port chamber. In some embodiments, operation of an indicator device is prompted in response to the determination of the presence of a needle within the port chamber. In other embodiments, the methods includes attempting to inject a liquid substantially at room temperature into the port chamber and then monitoring a sensed temperature of the port chamber to determine whether the injected liquid is being delivered to the port chamber, with the determination of the needle position being dictated by a sensed change in temperature of the port chamber.

Yet other aspects in accordance with principles of the present invention relate to a system for monitoring an implantable medical device including an implantable therapeutic substance delivery device for delivering a liquid therapeutic substance to a delivery site of a patient. The delivery device includes a housing maintaining a reservoir for containing the therapeutic substance, along with a fill port assembly. In this regard, the fill port assembly includes a septum disposed across a port chamber that is in fluid communication with the reservoir. In addition, the system further includes means for sensing information relating to a temperature of the port chamber and an indicator means. In this regard, the indicator means is electronically coupled to the sensing means and is adapted for indicating to a clinician information indicative of a needle being in the port chamber based upon information signaled from the sensing means. In one embodiment, the sensing means is a temperature sensor disposed within the port chamber at an interior side of the septum, and the indicator means is prompted by a detector means otherwise adapted to evaluate whether a temperature of the port chamber has decreased.

DETAILED DESCRIPTION OF THE INVENTION

Figure 1A:
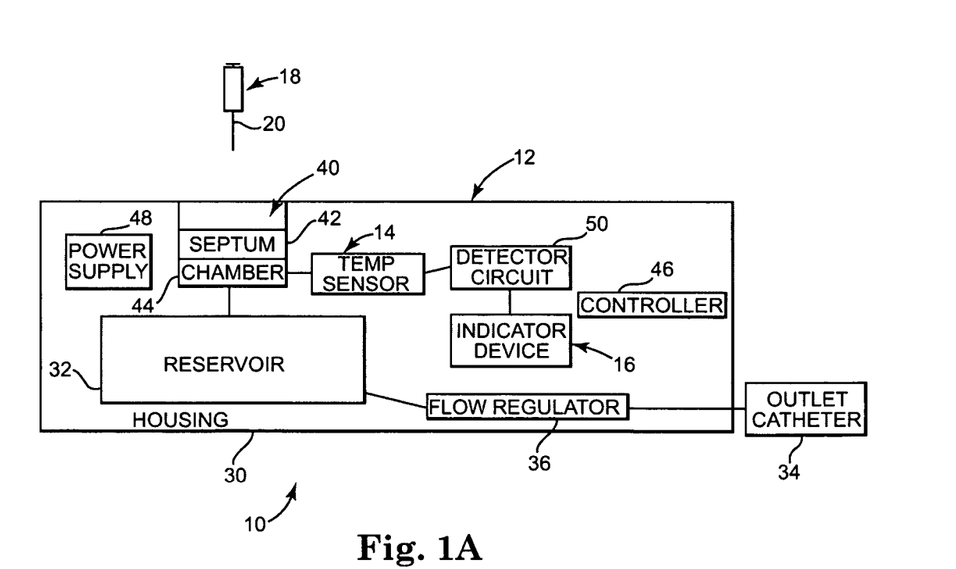
FIG. 1A is a block diagram depicting one system in accordance with principles of the present invention.

One embodiment of a system 10 in accordance with principles of the present invention is shown in block form in FIG. 1A. In general terms, the system 10 includes and is adapted to monitor an implantable therapeutic substance delivery device 12 as described below. In this regard, the system 10 further includes a temperature sensor 14 and an indicator device 16. Also depicted in FIG. 1A is a syringe assembly 18 including a needle 20 useful for percutaneously interfacing with the implantable delivery device 12 as described below.

The device 12 can be of any suitable, implantable design for temporarily storing and subsequently dispensing a liquid therapeutic substance (e.g., at a metered rate), such as a SynchroMed® EL implantable drug pump or an IsoMed™ constant flow infusion system, both available from Medtronic, Inc., of Minneapolis, Minn.; a Paradigm® insulin pump available from Medtronic-MiniMed, Inc., of Northridge, Calif.; etc. Further virtually any other implantable therapeutic substance delivery devices currently known or in the future contemplated can also be used in connection with principles of the present invention.

In general terms, the delivery device 12 includes a housing 30 that maintains a reservoir 32. The reservoir 32 contains the therapeutic substance (not shown) to be delivered to the patient, for example, via an outlet catheter 34. The therapeutic substance can be any infusion agent, product, or substance intended to have a therapeutic effect such as pharmaceutical compositions, genetic materials, biologics, and others (e.g., insulin, saline solution, fluoroscopy agents, etc.). Regardless, a pump and/or metering device (or "flow regulator") 36 can be provided for dictating a flow of the therapeutic substance from the reservoir 32 in a desired fashion. The pump/metering device 36 can assume a variety of forms, and the device 12 can further include a propellant chamber (not shown) associated with the reservoir 32 for exerting a constant, positive pressure onto the contained therapeutic substance to ensure delivery to the outlet catheter 34. In other embodiments, the pump/metering device 36 can be eliminated. Regardless, the delivery device 12 includes a fill port assembly 40 fluidly connected to, and otherwise defining an inlet of, the reservoir 32. One embodiment of the fill port assembly 40 is described in greater detail below. In more general terms, however, the fill port assembly 40 can assume a conventional configuration whereby a septum 42 seals a port chamber 44 relative to an exterior of the housing 30. The port chamber 44, in turn, is in fluid communication with the reservoir 32 (e.g., permanent fluid connection is established, a valve means is provided that actuates to selectively fluidly connect the port chamber 44 and the reservoir 32, etc.). With this configuration, then, the needle 20 can percutaneously deliver a liquid to the reservoir 32 upon insertion into the fill port assembly 40, and in particular through the septum 42 and into the port chamber 44, such as part of a reservoir refilling operation.

The delivery device 12 can further include a number of additional components as conventionally known. For example, the delivery device 12 can include a controller or electronics 46, for example in the form of a digital microprocessor, although any equivalent device may be substituted for a digital microprocessor; in many instances, it may also be desirable that the controller 46 includes data storage capabilities. Where provided, the controller 46 (as well as other components) can be powered by a power supply 48 (that may be preferably be the form of a battery or other self-contained power source). Other components can further be provided with the delivery device 12 that are not otherwise illustrated, such as safety valves, flow restrictors, etc., that may enhance operation of the delivery device 12.

With the above general construction of the delivery device 12 in mind, the temperature sensor 14 is maintained by the housing 30, and is associated with the fill port assembly 40. In some embodiments, and as described in greater detail below, the temperature sensor 14 is positioned adjacent or within the port chamber 44 of the fill port assembly 40. In one embodiment, the temperature sensor 14 signals sensed temperature-related information to a detector circuit 50 that in turn prompts operation of the indicator device 16. With the one embodiment of FIG. 1A, the detector circuit 50 and the indicator device 16 are maintained by the housing 30, with the detector circuit 50 adapted or programmed to prompt operation of the indicator device 16 based upon the temperature information generated and signaled by the temperature sensor 14. For example, the detector circuit 50 can be configured or programmed to prompt operation of the indicator device 16 upon determining (e.g., a logic circuit, a comparator, etc.) that the temperature sensed by the temperature sensor 14 (or as otherwise indicated by information signaled from the temperature sensor 14) is below a predetermined set point temperature, otherwise indicative of a room temperature liquid being dispensed into the port chamber 44, that in turn is indicative of the needle 20 being positioned within the port chamber 44, or more generally within the fill port assembly 40. Alternative techniques for detecting or concluding presence of the needle 28 within the port chamber 44 are described below. Regardless, with the one embodiment of FIG. 1A, the detector circuit 50 is shown as being a component apart from the controller 46. In other embodiments, however, the detector circuit 50 can be provided with the controller 46 such that the controller 46 is programmed to operate the indicator device 16 in a desired fashion. In yet other alternative embodiments, the detector circuit 50 can be eliminated.

Regardless of whether the indicator device 16 is acted upon by a circuit or controller apart from the temperature sensor 14, with the one embodiment of FIG. 1A, the indicator device 16 is a sound generating device adapted to produce audible noise (e.g., constant or pulsating tones, buzzer-like noise, etc.) at a frequency and decibel level sufficient to be audibly perceived by a clinician otherwise interfacing with the delivery device 12 through the patient's skin.

Figure 1B:
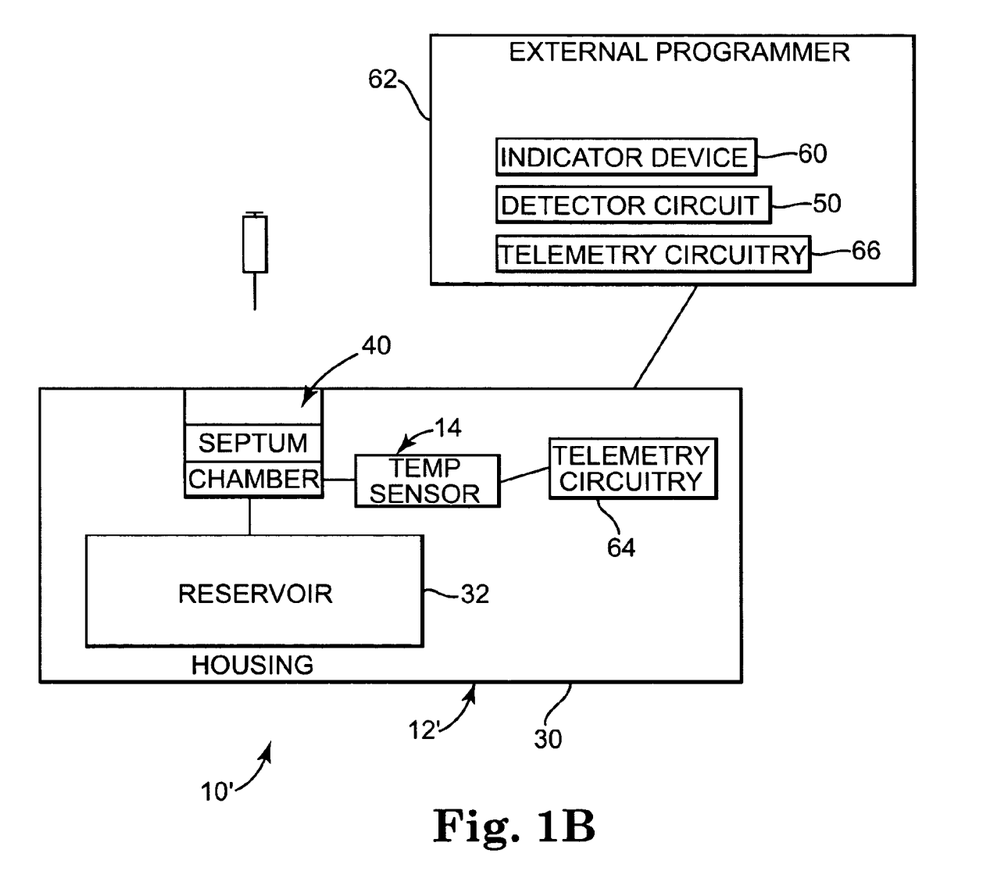
FIG. 1B is a block diagram illustrating an alternative embodiment system in accordance with principles of the present invention.

While the indicator device 16 has been described as being maintained by the housing 30, in alterative embodiments, the indicator device 16 can be provided apart from the housing 30 and/or a second indicator device (not shown) can be provided external the delivery device 12. For example, FIG. 1B is a block diagram representing an alternative embodiment system 10' in accordance with principles of the present invention. The system 10' is similar in many respects to the system 10, with like elements having like numbers. For example, the system 10' includes an implantable therapeutic substance delivery device 12' otherwise having the reservoir 32 fluidly connected to the fill port assembly 40. Further, the system 10' includes the temperature sensor 14 that is otherwise associated with the fill port assembly 40 as previously described. Finally, similar to the system 10, the system 10' includes an indicator device 60. However, with the embodiment of FIG. 1B, the indicator device 60 is located apart from the housing 30, for example as part of an external programmer 62. As is known in the art, the external programmer 62 is adapted to communicate with the delivery device 12' through the patient's skin such that in one embodiment, the external programmer 62 and the delivery device 12' are in wireless communication, for example via telemetry circuitry 64 maintained by the housing 30 and corresponding telemetry circuitry 66 maintained by the external programmer 62 (or a component (e.g., a hand-held instrument) electronically coupled to the external programmer 62). Alternatively, other forms of wireless communicative links between the delivery device 12' and the external programmer 62 can be provided.

Regardless, in one embodiment, the temperature sensor 14 is electronically coupled to the telemetry circuitry 64 (for example, via a controller (not shown)), with temperature-related information generated by the temperature sensor 14 being signaled to the external programmer 62 via the telemetry circuitries 64, 66. The external programmer 62 includes the detector circuit 50 previously described (that can be provided as part of a controller associated with the external programmer 62) that otherwise dictates operation of the indicator device 60. Once again, the parameters under which the detector circuit 50 will prompt operation of the indicator device 60 are described in greater detail below. In one embodiment, the indicator device 60 is a display screen adapted to display information to the clinician. As is known in the art, a display screen is commonly provided with the external programmer 62 (e.g., an N'Vision™ Programmer available from Medtronic, Inc., of Minneapolis, Minn. as part of the SynchroMed® EL Infusion System), and can display information in a variety of fashions, for example, with words, pictures, symbols, graphical information, etc. The indicator device 60 can further include a sound generator as previously described. Regardless, in one embodiment, upon determining that temperature-related information generated by the temperature sensor 14 is indicative of the needle 20 being within the fill port assembly 40, the detector circuit 50 prompts the indicator device 60 to so inform the clinician via the display screen and/or sound generating device. In other embodiments, the detector circuit 50 can be eliminated with the indicator device 60 simply displaying a current temperature reading provided by the temperature sensor 14; under these conditions, the clinician can make a self-evaluation as to whether the sensed and displayed temperature is indicative of desired needle placement.

Figure 2:
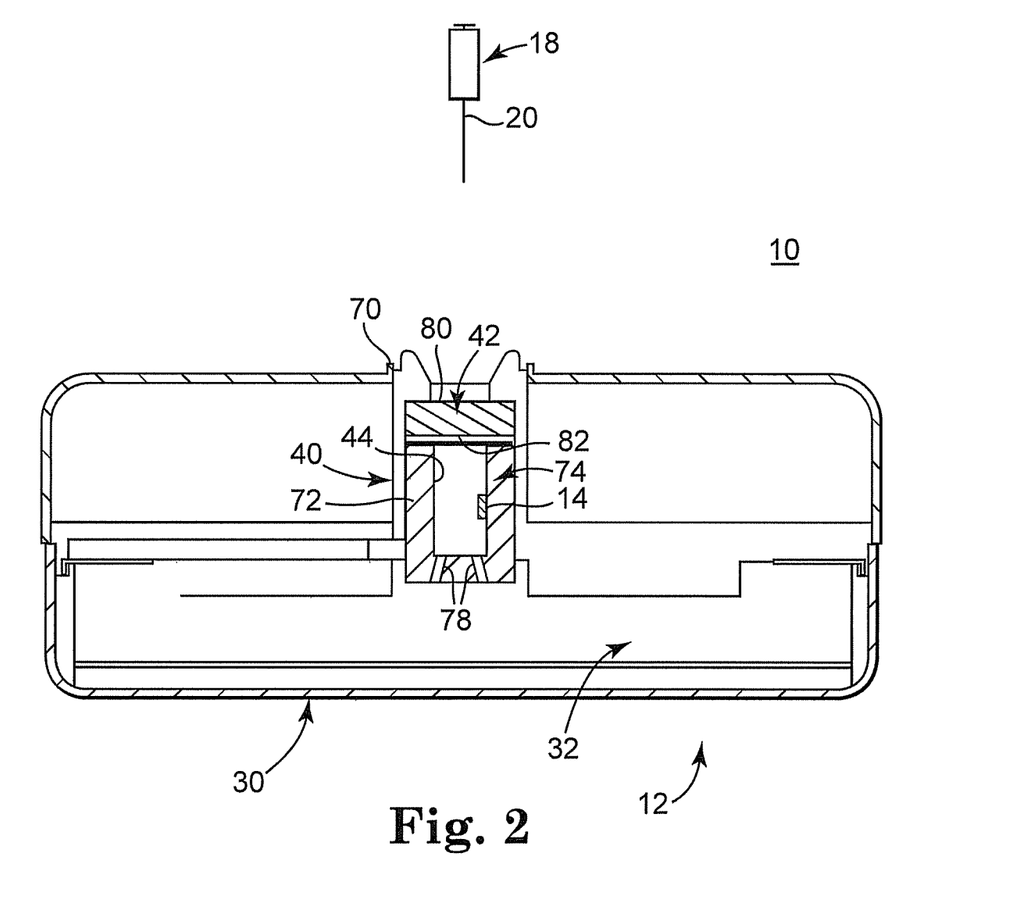
FIG. 2 is a cross-sectional view of a portion of an implantable therapeutic substance delivery device useful with the systems of FIGS. 1A and 1B.

FIG. 2 is a simplified, cross-sectional view of one embodiment of a portion of the system 10 in accordance with principles of the present invention, including the temperature sensor 14 in conjunction with relevant portions of the delivery device 12 including the housing 30, the reservoir 32, and the fill port assembly 40. In general terms, the fill port assembly 40 is formed in an opening 70 of the housing 30 such that the fill port assembly 40 is exteriorly accessible relative to the housing 30. The septum 42 is disposed across the port chamber 44 (referenced generally) defined by a wall 72 of the fill port assembly 40, such that the septum 42 seals the opening 70 relative to the port chamber 44/reservoir 32. The septum 42 can be manufactured of any suitable material or materials. Typically, the septum 42 will include elastomeric materials, for example, silicone rubber, that are pierceable by the needle 20 (FIG. 1A) (which itself does not necessarily form a part of the system 10) and compatible with the therapeutic substance (not shown) to be contained with the reservoir 32. In one embodiment, the fill port assembly 40 further includes a septum plug 74 used to retain the septum 42 while providing a fluid-tight seal. The septum plug 74 defines the port chamber 44 to include drain holes 78 that allow fluids delivered to the port chamber 44 to pass into the reservoir 32. In some embodiments, a valve feature (not shown) can be provided to further control flow of liquid from the port chamber 44 to the reservoir 32 as is known in the art. As a point of reference, relative to an arrangement of the fill port assembly 40, the septum 42 defines a first or exterior side and a second or interior side 82. The exterior side 80 is exposed relative to the opening 70 of the housing 30, whereas the interior side 82 defines a portion of the port chamber 44.

With the above conventions in mind, the temperature sensor 14 is, in one embodiment, associated with the fill port assembly 40, and in particular the port chamber 44, by disposing the temperature sensor 14 along an interior of a wall of the septum plug 74. In other embodiments, the temperature sensor 14 is disposed within a thickness of the septum plug 74 (such as by forming (e.g., overmolding) the septum plug 74 about the temperature sensor 14). Even further, the temperature sensor 14 can be assembled to an exterior of the septum plug 74 (relative to the port chamber 44).

Regardless of an exact location, the temperature sensor 14 can assume a variety of different forms. For example, the temperature sensor 14 can be a contact-type temperature sensor, such as a thermocouple, thermistor, resistance temperature detector (RTD), bimetallic sensor, etc. Alternatively, the temperature sensor 14 can be a noncontact-type sensor, such as an infrared thermometer, radiation thermometer, etc. Regardless, in one embodiment, the temperature sensor 14 is adapted to generate a signal indicative of a temperature of the port chamber 44. Alternatively, the temperature sensor 14 can be adapted to signal information indicative of a change in temperature of the port chamber 44. In more general terms, then, the temperature sensor 14 is any device capable of sensing and signaling information indicative of temperature characteristics associated with the port chamber 44 and/or the fluid port assembly 40 more generally. In this regard, the temperature sensor 14 can be electronically coupled to the detector circuit 50 (FIGS. 1A, 1B) and/or the indicator device 16 (FIG. 1A), 60 (FIG. 1B) in a variety of manners. For example, electrical wiring (not shown) can provide the desired electrical connection. Alternatively, a wireless link can be provided between the temperature sensor 14 and the processing device in question.

The system 10 as thus described (as well as system 10' of FIG. 1B) can be used to confirm placement of the needle 20 within the port chamber 44 and/or provide the clinician (not shown) with sufficient information to make this determination. In general terms, following implantation, a temperature of the delivery device 12 will approximately equilibrate with the body temperature of the patient. Thus, prior to a reservoir refilling procedure, a temperature of the port chamber 44, and thus a temperature sensed by the temperature sensor 14, will be greater than at least 90° F. In contrast, a temperature of the therapeutic substance otherwise maintained by the syringe assembly 18 is conventionally at a significantly lower temperature. For example, it is common practice for the therapeutic substance to be maintained at room temperature (i.e., on the order of 65°-75° F.) prior to injection into the delivery device 12. Thus, when the therapeutic substance is dispensed into the port chamber 44, the port chamber 44 will experience a reduction in temperature, with this reduced temperature (relative to body temperature) being sensed by the temperature sensor 14. Thus, a change (e.g., decrease) in temperature at or in the port chamber 44 is indicative of the needle 20 having been properly placed through the septum 42 and into the port chamber 44 prior to injection of the therapeutic substance. Conversely, when the needle 20 is not within the port chamber 44 (e.g., where the needle 20 has not pierced the septum 42, has not been positioned the needle 20 within the port chamber 44, etc.), the injected therapeutic substance will not flow into the port chamber 44, such that a temperature of the port chamber 44 (and thus the temperature sensed by the temperature sensor 14) will not change. This lack of change in port chamber temperature is thus indicative of the needle 20 not being properly positioned within the port chamber 44 during a refilling procedure.

Figure 3:
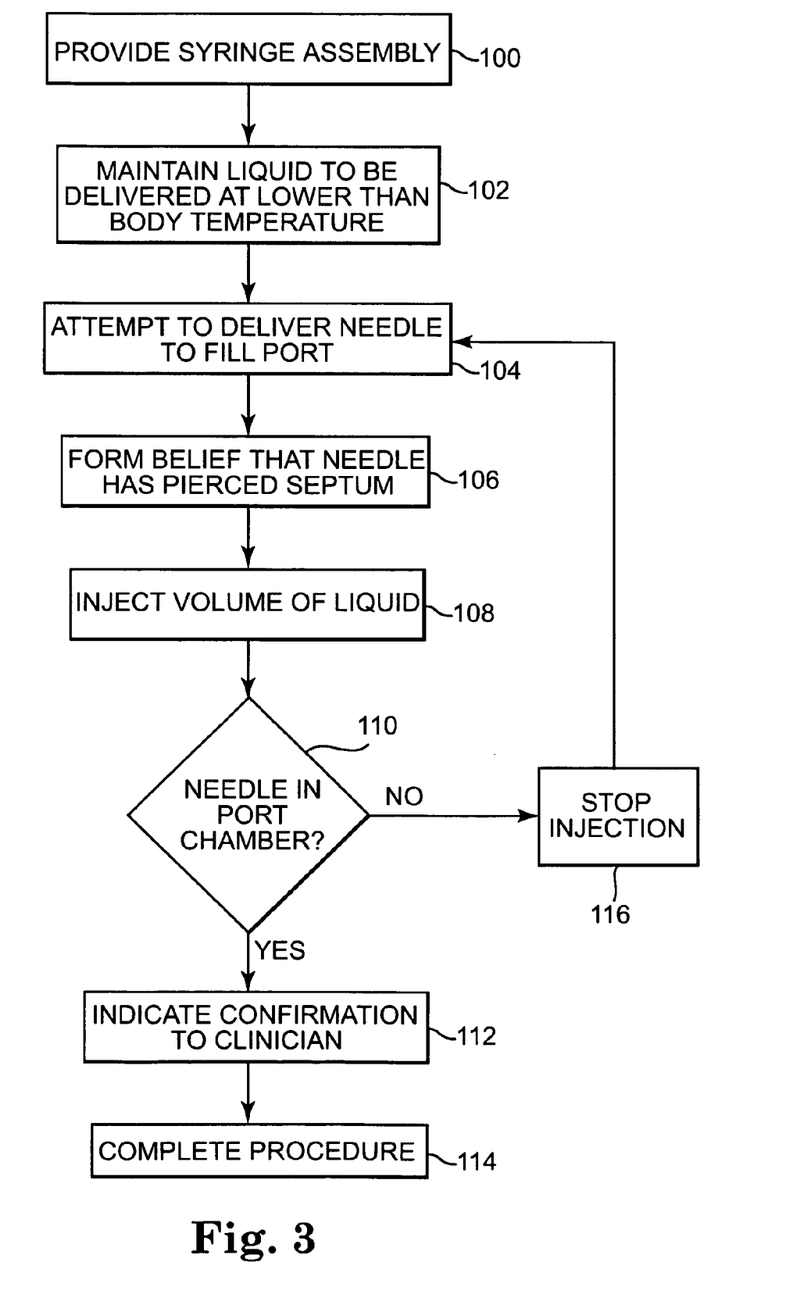
FIG. 3 is a flow chart of one method of monitoring an implantable therapeutic substance delivery device in accordance with principles of the present invention.

In light of the above, FIG. 3 provides a flow diagram illustrating one method of monitoring the delivery device 12 in accordance with principles of the present invention. In particular, FIG. 3 reflects a monitoring methodology as part of a percutaneous reservoir refilling procedure. Thus, the methodology relates to a scenario in which the delivery device 12 has previously been implanted and sufficient time has passed for the delivery device 12, and in particular the port chamber 44 to approach a body temperature of the patient.

With the above in mind and with additional reference to FIG. 2, at step 100, the syringe assembly 18 is provided. Once again, the syringe assembly 18 is of a conventional type, and includes the hypodermic needle 20 otherwise fluidly connected to a liquid (e.g., the therapeutic substance to be filled to the reservoir 32). The liquid to be delivered to the reservoir 32 is maintained at a lower temperature at step 102. In this regard, the liquid can be pre-loaded into the syringe assembly 18 in connection with assuring a desired temperature of the liquid. Alternatively, the liquid to be delivered can be stored at the desired temperature for a sufficient time period, and then loaded within the syringe assembly 18. Regardless, in one embodiment, step 102 entails the therapeutic liquid being provided at a temperature of no more than approximately 75° F. For example, in one embodiment, the liquid therapeutic substance is maintained at room temperature. In other embodiments, the liquid therapeutic substance to be delivered to the reservoir 32 is cooled below room temperature (e.g., temperature in the range of 50°-65° F.).

With the syringe assembly 18 loaded with the liquid therapeutic substance otherwise maintained at a desired temperature, at step 104 the clinician attempts to percutaneously deliver the needle 20 within the fill port assembly 40. In connection with this step, the clinician can utilize various techniques to best estimate a physical location of the fill port assembly 40 relative to the patient's skin prior to inserting the needle 20 (e.g., palpating a perimeter of the housing 30 through the patient's skin, use of a template, use of other port indicating devices, etc.). Regardless, at step 106, the clinician forms an opinion that the needle 20 has properly accessed the fill port assembly 40 and has pierced through the septum 42 so as to be positioned within the port chamber 44. Subsequently, at step 108, the clinician attempts to inject a volume of the liquid therapeutic substance through the needle 20.

At step 110, a determination is made, based upon information provided by the temperature sensor 14, as to whether the needle 20 is properly located within the port chamber 44. This determination can be made in a variety of fashions. For example, in one embodiment, a temperature being sensed by the temperature sensor 14 is displayed to the clinician (e.g., via the display screen/indicator device 60 associated with the external programmer 62 embodiment of FIG. 1B). Under circumstances where the clinician notices a decrease in sensed temperature following the injection of a small volume of the liquid therapeutic substance at step 108 (e.g., a decrease in temperature within 30-90 seconds of injection), the clinician can conclude that the liquid therapeutic substance is being delivered to the port chamber 44, and thus that the needle 20 is desirably located within the port chamber 44.

Alternatively, the detector circuit 50 (FIGS. 1A and 1B) can determine whether information signaled from the temperature sensor 14 is indicative of the liquid therapeutic substance being delivered within the port chamber 44, and thus of whether the needle 20 is located within the port chamber 44. For example, in one embodiment, the detector circuit 50 is adapted to compare whether the temperature-related information generated by the temperature sensor 14 is indicative of a temperature below a predetermined set point. To this end, the predetermined set point temperature can be an absolute value. With this embodiment, when the detector circuit 50 determines, via information from the temperature sensor 14, that a temperature of the port chamber 44 is below a certain value (e.g., a set point temperature of, for example, 85° F., 80° F., 75° F., etc.), the detector circuit 50 will automatically initiate a needle-in-septum operation. Alternatively, the predetermined set point value can be based upon a comparison of information signaled by the temperature sensor 14 immediately prior to initiation of the reservoir refill operation. For example, immediately prior to percutaneously inserting the needle 20, the clinician can indicate to the system 10, 10' (e.g., via the external programmer 62) that the refill procedure is about to begin. Upon receiving this indication, the detector circuit 50 ascertains and stores a current reading provided by the temperature sensor 14, with this reading then being used as the set point temperature. Subsequently, the detector circuit 50 continuously or periodically compares information from the temperature sensor 14 with this recorded value. Upon determining that the subsequently-generated temperature sensor information is indicative of a temperature of the port chamber 44 falling below this previously-recorded value (e.g., by 5° F. or more), the detector circuit 50 automatically determines that the liquid therapeutic substance is being delivered to the port chamber 44, and thus that the needle 20 is properly located within the port chamber 44.

In yet other embodiments, the detector circuit 50 operates to monitor information signaled from the temperature sensor 14 for a decrease in temperature over a predetermined time period (e.g., 30-90 seconds); under circumstances where the rate of temperature change and/or absolute temperature exceeds a predetermined value, the detector circuit 50 automatically initiates a needle-in-septum operational protocol. Alternatively and/or in addition, other techniques can be employed by the detector circuit 50 to determine whether information being generated by the temperature sensor 14 is indicative of the needle 20 being within the port chamber 44 in conjunction with the initial delivery of a small volume of the liquid therapeutic substance.

Relative to embodiments in which the system 10, 10' includes the detector circuit 50 (FIGS. 1A and 1B), upon determining that the information generated by the temperature sensor 14 is indicative of the needle 20 being within the port chamber 44, at step 112, the detector circuit 50 prompts the indicator device 16 (FIG. 1A), 60 (FIG. 1B) to perform a needle-in-septum operation or protocol. For example, in one embodiment in which the indicator device 16 (FIG. 1A) is a sound generator carried by the housing 30, the needle-in-septum protocol includes causing the sound generator 16 to generate an audible noise. In one embodiment, the audible noise is a series of tones; in other embodiments, the audible noise is a buzzer. Further, other sounds understood by a clinician to indicate the presence of a needle within the port chamber 44 can alternatively be provided. To this end, the system 10, 10' can be adapted such that the on-board sound generator 16 produces a first sound/series of sounds upon receiving an indication from a clinician that a reservoir refilling procedure is about to begin, and a second, different sound/series of sounds upon being prompted by the detector circuit 50 (under circumstances in which the detector circuit 50 otherwise determines that information from the temperature sensor 14 is indicative of the needle 20 being within the port chamber 44). Under these circumstances, then, where the clinician does not perceive a change in the sounds being generated by the indicator device 16, the clinician can then conclude that the needle 20 was not properly placed or inserted within the port chamber 44. In yet even other embodiments, and in particular with the system 10' of FIG. 1B, the needle-in-septum operational protocol includes generating a display on the display screen/indicator device 60 of a type that a clinician will perceive as indicating that the needle 20 is properly located within the port chamber 44. Once again, this confirmation can be in the form of words, symbols, pictures, etc.

Regardless of how the information is provided with the clinician, at step 114 the clinician acts upon the confirmation of the needle 20 being properly located within the port chamber 44, and completes the refilling procedure. Alternatively, if at step 110 it is concluded that the needle 20 is not within the port chamber 44, at step 116, the clinician acts upon this information, and decides to stop the refilling procedure. From this point, the method returns to step 104 at which the clinician re-attempts to percutaneously delivery the needle 20 the fill port assembly 40. The method then continues as previously described, with the clinician awaiting confirmation of the needle 20 being properly located within the port chamber 44 before completing the refilling operation.

The monitoring system and method of the present invention has been described above in connection with use of information from the temperature sensor 14. In other embodiments, a sensor other than a temperature sensor can be employed. In general terms, and with reference to FIG. 4A, an alternative embodiment system 130 in accordance with aspects of the present invention includes the delivery device 12 as previously described, along with a sensor 132 and the indicator device 16 or 60. Once again, the indicator device 16, 60 can be provided as part of the housing 30 (e.g., akin to the embodiment described with respect to FIG. 1A), or as part of an external programmer (such as the external programmer 62 of FIG. 1B). Further, in some embodiments, a detector circuit 134 is electronically coupled to the sensor 132, and uses information signaled from the sensor 132 to determine whether the needle 20 has been properly placed within the fill port assembly 40.

Figure 4A:
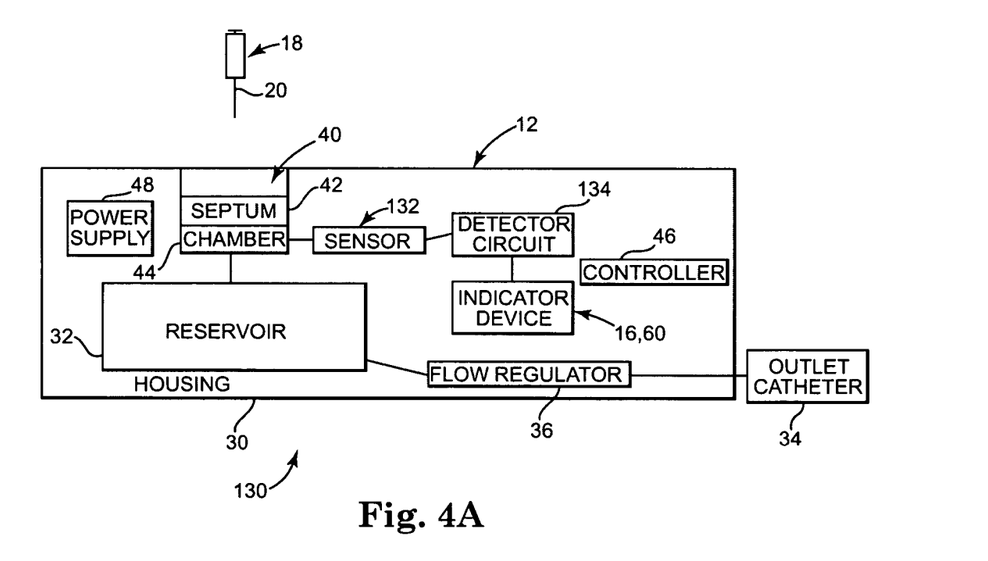
FIG. 4A is a block diagram illustrating an alternative embodiment system in accordance with principles of the present invention.
Figure 4B:
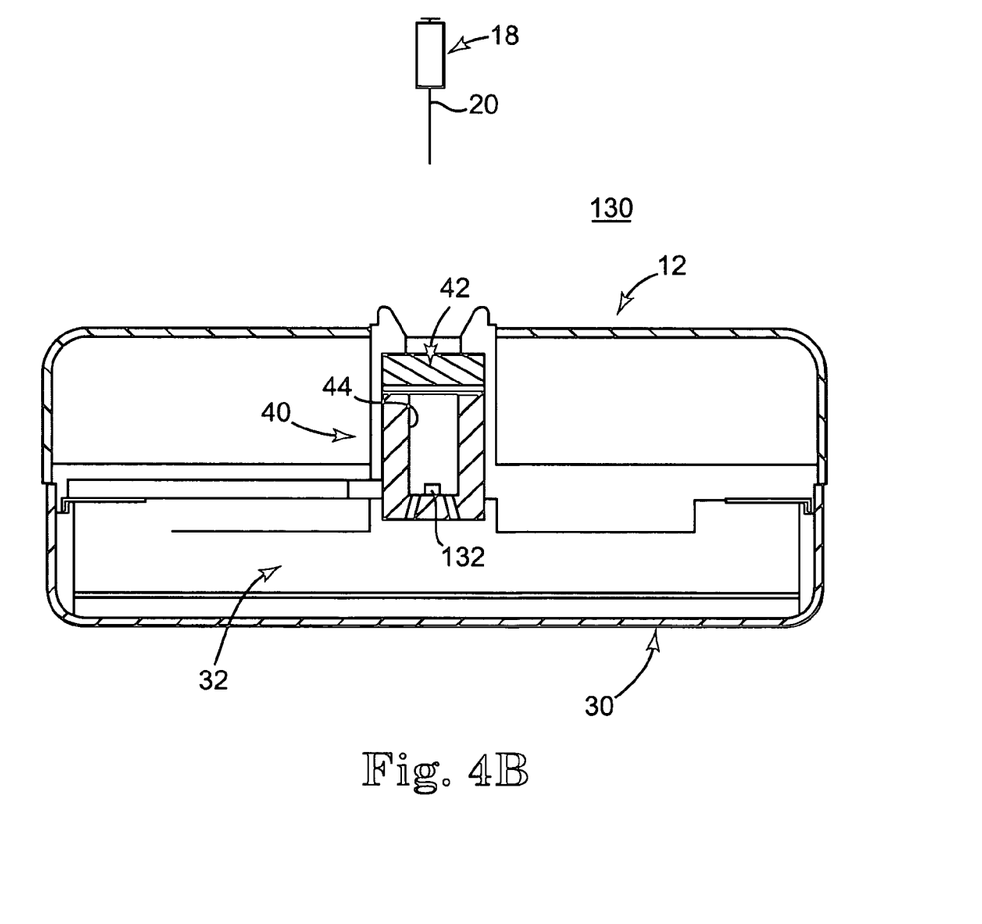
FIG. 4B is a cross-sectional view of a portion of an implantable therapeutic substance delivery device useful with the system of FIG. 4A.

With the above general configuration in mind, and with additional reference to FIG. 4B, the sensor 132 is a pressure sensitive switch installed at the bottom of the port chamber 44 (or other structure defining a bottom of the fill port assembly 40). With this configuration, any force applied by the needle 20 serves to close the switch circuit, thus allowing the detector circuit 134 (FIG. 4A) to receive an indication that the needle 20 is within the port chamber 44. With this determination in hand, the detector circuit 50 (FIG. 4A) can then operate the indicator device 16, 60 (FIG. 4A) as previously described. The pressure sensitive switch or sensor 132 can assume a variety of forms, including a bending beam contact switch, a capacitive sensor with a spring-loaded plate, a piezoelectric sensor, etc.

In yet another alternative embodiment, the sensor 132 is a wire mesh molded into the middle of the septum 42, with the wire mesh having an opening size slightly smaller than the size of a typical hypodermic needle otherwise used in connection with a reservoir refilling operation. When the needle 20 passes through the mesh and makes contact with the bottom of the port chamber 44 (or other structure defining a bottom of the fill port assembly 40), a switch circuit would be completed, allowing the detector circuit 134 (FIG. 4A) to sense or determine that the needle 20 is present within the port chamber 44. In a related, alternative embodiment, two separate layers of mesh could be formed within the septum 42, such that upon insertion of the needle 20 through the two mesh layers, a circuit path is completed between them, once again allowing the detector circuit 134 to sense the presence of the needle 20 within the port chamber 44.

In yet another alternative embodiment, the sensor 132 is a pressure sensor located within the port chamber 44, and configured to indicate when a pressure within a port chamber 44 has increased. This increase in pressure is indicative of a liquid being injected into the port chamber 44 (with this pressure increase more readily being identified when a slight flow restriction between the fill port assembly 40 and the reservoir 32 is provided). Under these circumstances, the detector circuit 134 can effectively sense the presence of the needle 20 within the port chamber 44, and cause the indicator device 16, 60 to operate as previously described.

The system and method of the present invention provides a marked improvement over previous designs. In one embodiment, by assessing needle-in-septum placement based upon temperature changes within the septum chamber, the system and method of the present invention provides the clinician with important feedback information based on the presence (or absence thereof) of actual therapeutic substance within the port chamber itself. Thus, regardless of which technique(s) a clinician employs to initially estimate fill port location, an after-the-fact confirmation of needle placement is provided.

Although the present invention has been described with reference to preferred embodiments, workers skilled in the art will recognize that changes can be made in form and detail without departing from the spirit and scope of the present invention.

What is claimed is:

1. A system for monitoring an implantable medical device, the system comprising:
an implantable liquid therapeutic substance delivery device for delivering a therapeutic substance to a delivery site within a patient, the device including:
a housing maintaining a reservoir for containing the therapeutic substance,
a fill port assembly defining a port chamber in fluid communication with the reservoir, the fill port assembly further including a septum fluidly sealing the port chamber relative to an exterior of the device;
a temperature sensor positioned to sense a temperature of the port chamber; and
an indicator device for indicating presence of liquid dispensed from a needle disposed within the port chamber based upon information from the temperature sensor.

2. The system of claim 1, wherein the port chamber is fluidly open to the reservoir, and further wherein the temperature sensor is positioned within the port chamber.

3. The system of claim 2, wherein the temperature sensor is configured to sense a change in a temperature of the port chamber.

4. The system of claim 1, wherein the temperature sensor is adapted to sense presence of a liquid maintained at room temperature being infused into the port chamber.

5. The system of claim 1, wherein the indicator device is adapted to generate at least one of an audible and visual indication to a clinician of the presence of a needle within the port chamber.

6. The system of claim 5, wherein the indicator device includes a sound generator maintained by the housing.

7. The system of claim 5, further comprising:
an external programmer provided apart from the delivery device and adapted to wirelessly communicate with the delivery device;
wherein the indicator device includes a display screen associated with the external programmer.

8. The system of claim 5, wherein the indicator device is programmed to display temperature information as a function of temperature information signaled by the temperature sensor.

9. The system of claim 8, wherein the indicator device is adapted to display a current temperature sensed by the temperature sensor.

10. The system of claim 8, wherein the indicator device is adapted to display a change in a temperature sensed by the temperature sensor on a display screen.

11. The system of claim 1, further comprising:
a detection circuit adapted to detect the presence of a needle in the port chamber based upon information from the temperature sensor and to prompt operation of the indicator device.

12. The system of claim 11, wherein the detection circuit is adapted to compare a current temperature sensed by the temperature sensor with a set point temperature.

13. The system of claim 12, wherein the set point temperature is a predetermined value.

14. The system of claim 12, wherein the set point temperature is a previous temperature sensed by the temperature sensor.

15. The system of claim 12, wherein the detection circuit is adapted to prompt operation of the indicator device upon determining that the current temperature is less than the set point temperature.

16. The system of claim 12, wherein the detection circuit is adapted to prompt operation of the indicator device upon determining that the current temperature is decreasing relative to the set point temperature over a predetermined time period.

17. A method of monitoring an implantable therapeutic substance delivery device, the method comprising:
providing an implantable liquid therapeutic substance delivery device for delivering a therapeutic substance to a delivery site within a patient, the delivery device including:
a housing maintaining a reservoir for containing the therapeutic substance;
a fill port assembly including a port chamber in fluid communication with the reservoir, the fill port assembly further including a septum disposed across the port chamber to fluidly seal the port chamber relative to an exterior of the device;
a temperature sensor positioned to sense a temperature of the port chamber;
providing an indicator device for indicating presence of liquid dispensed from a needle within the port chamber based upon information from the sensor;
sensing information relating to a temperature of the port chamber; and determining whether the sensed information is indicative of a presence of a needle within the port chamber.

18. The method of claim 17, further comprising:
controlling the indicator device based upon the determination.

19. The method of claim 18, wherein controlling the indicator device includes prompting operation of the indicator device upon determining that the sensed information is indicative of a presence of a needle within the port chamber.

20. The method of claim 18, wherein the indicator device includes a sound generator maintained by the housing.

21. The method of claim 18, wherein the indicator device includes a display screen provided as part of an external programmer in wireless communication with the delivery device.

22. The method of claim 21, wherein prompting operation of the indicator device includes causing the display screen to display a current temperature sensed by the temperature sensor.

23. The method of claim 21, wherein prompting operation of the indicator device includes causing the display screen to display a change in a temperature sensed by the temperature sensor over time.

24. The method of claim 17, wherein determining whether the sensed information is indicative of a presence of a needle within the port chamber is based upon a determination that a liquid at a temperature below a temperature of the delivery device is being injected into the port chamber.

25. The method of claim 17, wherein determining whether the sensed information is indicative of a presence of a needle with the port chamber includes: comparing a currently sensed temperature with a set point temperature.

26. The method of claim 18, wherein determining whether the sensed information is indicative of a presence of a needle within the port chamber includes:
    recording a first temperature sensed by the temperature sensor as the set point temperature;
    wherein a currently sensed temperature is obtained after recording the first temperature.

27. The method of claim 17, further comprising:
    providing a syringe assembly including a needle fluidly connected to a supply of liquid;
    maintaining the supply of liquid at a temperature below 85° F.;
    attempting to percutaneously access the port chamber with the needle;
    injecting a volume of the liquid through the needle; and
    sensing a decrease in temperature at the temperature sensor when the needle is within the port chamber immediately after the step of injecting the volume of liquid.

28. The method of claim 27, wherein a decrease in temperature is not sensed at the temperature sensor immediately after the step of injecting a volume of liquid when the needle is not located within the port chamber during the step of injecting a volume of liquid through the needle.

29. The method of claim 27, wherein immediately prior to the step of percutaneously accessing the port chamber, the liquid is stored at approximately room temperature and the port chamber has a temperature approximating a bodily temperature of the patient.

30. A system for monitoring an implantable medical device, the system comprising:
    an implantable liquid therapeutic substance delivery device for delivering a liquid therapeutic substance to a delivery site of a patient, the delivery device including:
        a housing maintaining a reservoir for containing the therapeutic substance;
        a fill port assembly including a septum exteriorly fluidly sealing a port chamber otherwise in fluid communication with the reservoir;
        an outlet catheter extending from the housing and fluidly connected to the reservoir;
    means carried by the housing for sensing information relating to a temperature of the port chamber; and
    indicator means electronically coupled to the sensing means for selectively indicating to a clinician information indicative of one of:
        absence of a needle in the port chamber, and
        presence of a needle and liquid dispensed therefrom in the port chamber,
        based upon information signaled from the sensing means.

31. The system of claim 30, wherein the sensing means is a temperature sensor.

32. The system of claim 30, further comprising:
    a source of liquid therapeutic substance at a temperature in the range of 50°-65° F. for refilling the reservoir.

* * * * *